(12) United States Patent
Apicella et al.

(10) Patent No.: US 6,887,483 B2
(45) Date of Patent: May 3, 2005

(54) NON-TOXIC MUTANTS OF PATHOGENIC GRAM-NEGATIVE BACTERIA

(75) Inventors: Michael A. Apicella, Solon, IA (US); Melvin G. Sunshine, Iowa City, IA (US); Na-Gyong Lee, Incheon (KR); Bradford W. Gibson, Berkeley, CA (US)

(73) Assignees: University of Iowa Research Foundation, Iowa City, IA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 08/565,943

(22) Filed: Dec. 1, 1995

(65) Prior Publication Data

US 2005/0048076 A1 Mar. 3, 2005

(51) Int. Cl.$^7$ ..................... A61K 39/102; A61K 39/02; C12N 1/20; C07K 16/00
(52) U.S. Cl. ............................... 424/256.1; 424/200.1; 424/234.1; 435/69.3; 435/252.3; 530/390.1
(58) Field of Search .......................... 424/176.1, 200.1, 424/236.1, 256.1; 435/170, 243, 252.3, 69.3; 530/390.1; 935/66, 72

(56) References Cited

U.S. PATENT DOCUMENTS

| | | | | |
|---|---|---|---|---|
| 4,912,094 A | * | 3/1990 | Myers et al. | 514/54 |
| 4,929,604 A | | 5/1990 | Munford et al. | 514/53 |
| 5,200,184 A | * | 4/1993 | Munford et al. | 424/94.61 |
| 5,641,492 A | | 6/1997 | Sprouse et al. | 424/258.1 |
| 6,482,807 B1 | * | 11/2002 | Van der Ley et al. | 514/54 |
| 6,548,287 B1 | * | 4/2003 | Powell et al. | 435/243 |

FOREIGN PATENT DOCUMENTS

| | | | | |
|---|---|---|---|---|
| WO | 97/18837 | | 5/1997 | ......... A61K/39/02 |
| WO | WO 97/19688 | * | 5/1997 | |

OTHER PUBLICATIONS

Raetz CRH. Annu. Rev. Biochem. 59: 129–170, 1990.*
Jachymek W. Post. Hih. Med. Dosw. 49: 1: 171–178, 1995.*
Kulshin et al., J. Bacteriol. 174: 1793–1800, 1992.*
Westphal et al. Methods in Carbohydr. Chem. 5: 83–91, 1965.*
McLaughlin et al. J. Bacteriol. 174: 6455–6459, 1965.*
Brooks et al. Jawetz, Melnick & Adelberg's Medical Microbiology 20$^{th}$ ed. 1995.*
Karow, Margaret Lee. Molecular Genetics of the *Escherichia coli* HtrB gene. (Dissertation, 1992).*
Karow et al Journal of Bacteriology 174(22): 7407–7418, 1992.*
Lehmann et al. Eur. J. Biochem 178:459–464, 1988.*
Lee et al. Journal of Bio.*
Hitchock et al. "Morphological Heterogeneity Among *Salmonella* Lipopolysaccharide Chemotypes in Silver–Stained Polyacrylamide Gels", Journal of Bacteriology, Apr. 1983, pp 269–277 vol. 154 No. 1.*

Golenbock, D.T., et al., "Lipid A–like molecules that antagonize the effects of endotoxins on human monocytes", *J. of Biological Chemistry, 266* (29), pp. 19490–19498, (1991).

Lee, N., et al., "Mutation of the htrB Locus of Haemophilus influenzae Nontypable Strain 2019 Is Associated with Modifications of Lipid A and Phosphorylation of the Lipo–oligosaccharide", *J. Biol. Chem., 270* (45). pp. 27151–27159, (1995).

Raetz, C. R., "Bacterial Endotoxins: Extraordinary lipids that activate eucaryotic signal transduction", *J. of Bacteriology, 175* (18), pp. 5745–5753, (Sep. 1993).

Gupta, R.K., et al., "Synthesis, characterization, and some immunological properties of conjugates composed of the detoxifiedlipopolysaccharide of vibrio cholerae 01 serotype inaba bound to cholera toxin", *Infection and Immunity, 60, 8*, 3201–3208 (1992).

Karow, M., et al., "Sequencing, mutational analysis, and transcriptional regulation of the *Escherichia coli* htrB gene", *Molecular Microbiology, 5, 9*, 2285–2292 (1991).

Karow, M., et al., "Isolation and Characterization of the *Escherichia coli* htrB gene, whose product is essential for bacterial viability above 33degreesC in rich media", *Journal of Bacteriology*, vol. 173, No. 2, pp. 741–750, (Jan. 1991).

Karow, M., et al., "The lethal Phenotype 'caused by null mutations in the *escherichia coli* htrB gene is suppressed by Mutations in the accBC Operon, Encoding two subunits of acetyl coenzyme A carboxylase", *Journal of Bacteriology*, vol. 174, No. 22, pp. 7407–7418, (Nov. 1992).

Lee, N., et al., "Mutation of the htrB locus of Haemophilus influenzae nontypable strain 2019 is associated with modifications of lipid A and physophorylation of the lipo–oligosaccharide", *The Journal of Biological Chemistry*, vol. 270, No. 45, pp. 27151–27159, (Nov. 10, 1995).

Karow et al., "The Lethal Phenotype Caused by Null Mutations in the *Escherichia coli* htrB Gene is Suppressed by Mutations in the *accBC* Operon, Encoding Two Subunits of Acetyl Coenzyme A Carboxylase" Journal of Bacteriology, vol. 174, No. 22, 11/92, pp. 7407–7418.

* cited by examiner

Primary Examiner—S. Devi
(74) Attorney, Agent, or Firm—Fish & Richardson P.C., P.A.

(57) ABSTRACT

A method is provided for identifying, isolating, and producing htrB mutants of gram-negative bacterial pathogens. The method comprises mutating the htrB gene of a gram-negative bacterial pathogen so that there is a lack of a functional HtrB protein, resulting in a mutant that lacks one or more secondary acyl chains and displays substantially reduced toxicity as compared to the wild type strain. Also, the present invention provides methods for using a vaccine formulation containing the htrB mutant, or the endotoxin isolated therefrom, to immunize an individual against infections caused by gram-negative bacterial pathogens by administering a prophylactically effective amount of the vaccine formulation.

5 Claims, 3 Drawing Sheets

And/Or

NON-TOXIC MUTANTS OF PATHOGENIC GRAM-NEGATIVE BACTERIA

This invention has been made with government support under grant AI 24616 awarded by the National Institutes of Health. The government has certain rights in the invention.

FIELD OF THE INVENTION

The present invention relates to compositions comprising altered endotoxin) (lipooligosaccharide (LOS); lipopolysaccharide (LPS)) of gram-negative bacterial pathogens. More particularly, the present invention relates to the making of a form of endotoxin, by a genetically engineered gram-negative pathogen, which lacks a substantially toxic lipid A portion. Also disclosed are prophylactic and therapeutic uses of the substantially detoxified endotoxin, and of mutant gram-negative bacteria producing the substantially detoxified endotoxin.

BACKGROUND OF THE INVENTION

Gram-negative bacteria have an outer membrane comprised of components including proteins, lipoproteins, phospholipids, and glycolipids. The glycolipids comprise primarily endotoxin-lipopolysaccharides (LPS) or lipooligosaccharides (LOS), depending on the genus of bacteria. LPS are molecules comprised of
a) a lipid A portion which consists of a glucosamine disaccharide that is substituted with phosphate groups and long chain fatty acids in ester and amide linkages;
b) a core polysaccharide which is attached to lipid A by an eight carbon sugar, KDO (ketodeoxyoctonoate), and heptose, glucose, galactose, and N-acetylglucosamine; and
c) an O-specific side chain comprised of repeating oligosaccharide units which, depending on the genera and species of bacteria, may contain mannose, galactose, D-glucose, N-acetylgalactosamine, N-acetylglucosamine, L-rhamnose, and a dideoxyhexose (abequose, colitose, tyvelose, paratose, trehalose). LOS has a similar structure as LPS, containing a lipid A portion and a complex carbohydrate structure, but differs in that it does not contain repeating O-side chains.

The major antigenic determinants of gram-negative bacteria are believed to reside in the carbohydrate structure of the O-specific side chain of LPS and the complex carbohydrate structure of LOS. These carbohydrate structures may vary for different species of the same genera of gram-negative bacteria by varying one or more of the sugar composition; the sequence of oligosaccharides; the linkage between the oligosaccharides; and substitutions/modifications of an oligosaccharide (particularly a terminal oligosaccharide).

LPS and LOS have been considered as bacterial components which have potential as vaccine immunogens because of the antigenic determinants ("epitopes") residing in their carbohydrate structures. However, the chemical nature of LPS and LOS prevent the use of these molecules in vaccine formulations; i.e., active immunization with LPS or LOS is unacceptable due to the inherent toxicity of the lipid A portion. The pathophysiologic effects induced (directly or indirectly) by lipid A of LPS or LOS in the bloodstream include fever; leucopenia; leucocytosis; the Shwartzman reaction; disseminated intravascular coagulation; abortion; and in larger doses, shock and death. Accordingly, there are no currently available vaccines which induce antibody responses to LPS or LOS epitopes.

As shown in FIG. 1, the lipid A portion of endotoxin generally comprises a hydrophilic backbone of glucosamine disaccharide which is either monophosphorylated or diphosphorylated (positions 1 and 4'); and which carries at least six molecules of ester- and amide-bound fatty acids. Four molecules of (R) 3-hydroxytetradecanoate (e.g. 3-hydroxymyristoyl or β-hyroxymyristic acid or β-OH) are linked directly to the lipid A backbone at positions 2, 3, 2', and 3'. Hydroxyl groups of two of the four molecules of β-OH are substituted with normal fatty acids (termed "secondary acyl chains", and including dodecanoate, tetradecanoate, and hexadecanoate) in forming acyloxyacyl groups.

One approach to making a detoxified endotoxin molecule involves isolating the endotoxin, and enzymatically-treating the isolated endotoxin with a human neutrophilic acyloxyacyl hydrolase (U.S. Pat. Nos. 4,929,604, 5,013,661 and 5,200,184). The acyloxyacyl hydrolase hydrolyzes the fatty acids (non-hydroxylated, secondary acyl chains) from their ester linkages to hydroxy groups of β-OH (hydroxylated). The resultant altered endotoxin, from enzymatic treatment, contained a lipid A moiety lacking non-hydroxylated fatty acids. This altered endotoxin exhibited reduced in vivo toxicity, but retained antigenicity.

Another approach involves a method of modifying isolated endotoxin by selectively removing the β-OH that is ester-linked to the reducing-end glucosamine backbone at position 3 (U.S. Pat. No. 4,912,094; Reexamination B1 4,912,094). The selective removal of β-OH was accomplished using alkaline hydrolysis. The resultant modified endotoxin exhibited reduced in vivo toxicity, but retained antigenicity.

Both approaches involve chemically treating isolated endotoxin. Neither approach discloses the production in a gram negative bacterial pathogen of an endotoxin having substantially reduced toxicity, yet retaining antigenicity. Further, there has been no disclosure of the use of a gram-negative bacteria, which has been engineered to produce an endotoxin having substantially reduced toxicity and yet retaining antigenicity, in a prophylactic or therapeutic vaccine against endotoxic shock and gram-negative bacteremia.

SUMMARY OF THE INVENTION

The present invention is directed to a method for producing, in a mutant gram-negative pathogen, LPS or LOS which exhibits substantially reduced toxicity as compared to the wild type endotoxin, and which retains the antigenicity of its corresponding wild type endotoxin. The method comprises creating a mutation in the htrB gene of the gram-negative bacterial pathogen such that there is a lack of functional HtrB protein in the mutated gram-negative bacterial pathogen. It was found that lipid A produced by the htrB mutant lacks one or both of the fatty acids (non-hydroxylated or secondary acyl chains) thereby rendering the endotoxin in an isolated form, or the mutant gram-negative bacterial pathogen bearing the endotoxin, substantially reduced in toxicity and yet retaining antigenicity, as compared to wild type. Endotoxin isolated from htrB mutants or the htrB mutants themselves (whole cell vaccine), can be used to immunize individuals at risk of gram-negative bacteremia by inducing antibodies to the major antigenic determinants which reside in the carbohydrate structure of the O-specific side chain of LPS and the complex carbohydrate structure of LOS. Further, the htrB mutants can be engineered to express heterologous antigens of other microbial pathogens at the surface of the htrB mutant for presentation to a vaccinated individual's immune system in a multivalent vaccine. Also, the endotoxin isolated from the htrB mutants of the present invention may be used to generate LPS or LOS-specific antibody which may be useful for passive immunization and as reagents for diagnostic assays directed to detecting the presence of gram-negative bacterial pathogens in clinical specimens.

DETAILED DESCRIPTION OF THE INVENTION

Figure 1:
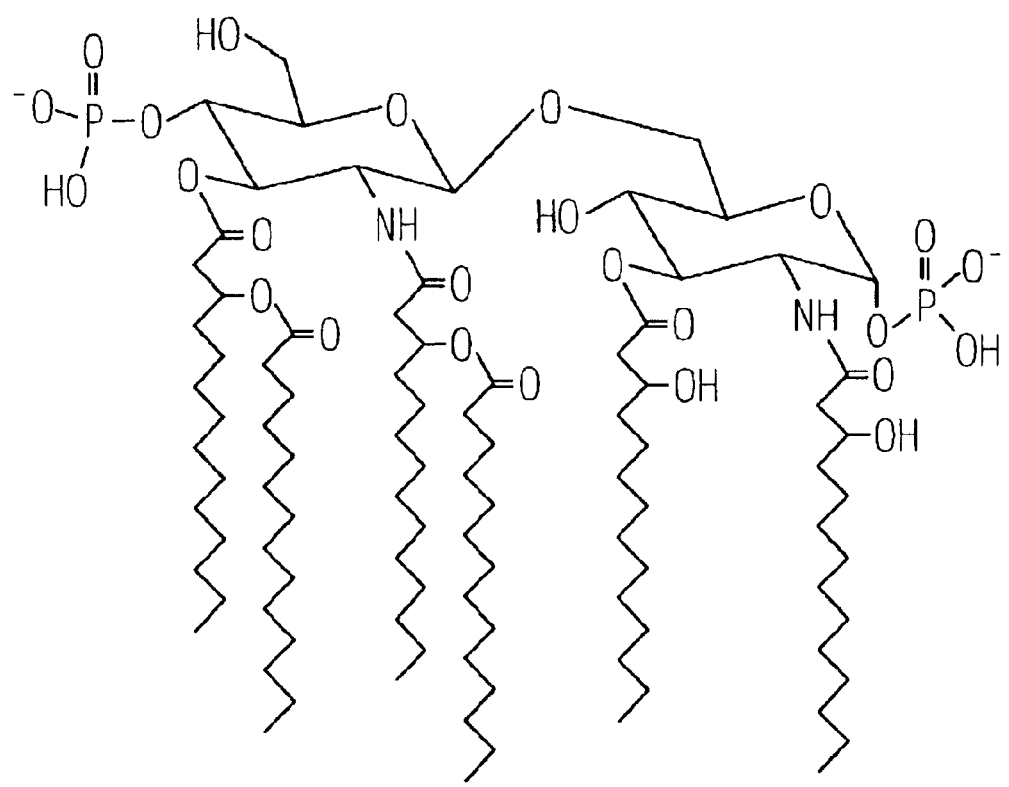
FIG. 1 is a schematic representation of the general structure of lipid A of gram negative bacteria of the family Enterobacteriaceae.

Definitions:

"Endotoxin" is a term used herein for purposes of the specification and claims to refer to the LPS or LOS of gram-negative bacterial pathogens, wherein the endotoxin is either in a cell-associated or isolated form. "htrB endotoxin" refers to endotoxin isolated and purified from an gram-negative bacterial pathogen htrB mutant".

"vaccine candidate or vaccine antigen" is a term used herein for purposes of the specification and claims to refer to an antigen having one or more of the following properties (a–d): (a) is immunogenic; (b) is surface-exposed (which can be shown by techniques known in the art including immunofluorescence assays, electron microscopy staining procedures, and by bactericidal assays); (c) induces antibody having bactericidal activity in the presence of complement and/or functions in immune clearance mechanisms; (d) induces antibody which neutralizes other functional activity of the epitope (immunogenicity, or toxicity, etc.).

"Gram-negative bacterial pathogen" is a term used herein for the purposes of the specification and claims to refer to one or more pathogenic (to humans or animals) bacterium of a genus and species including *Neisseria meningitidis, Neisseria gonorrhoeae, Haemophilus influenzae, Haemophilus ducreyi*, other *Haemophilus* species, *Moraxella catarrhalis, Campylobacter jejuni, Salmonella typhimurium*, other *Salmonella* species, *Shigella dysentariae*, and other *Shigella* species, and *Pseudomonas aeruginosa*.

"Substantially reduced in toxicity" is a term used herein for the purposes of the specification and claims to refer to a reduction in bioactivity of at least 10 fold to 100 fold as compared to wild type endotoxin.

The methods and compositions of the present invention relate to LPS and LOS biosynthetic pathways of gram-negative bacterial pathogens. More specifically, the present invention relates to mutations in the htrB gene of gram-negative bacterial pathogens resulting in mutant bacteria bearing endotoxin which is substantially reduced in toxicity, and yet retains antigenicity, as compared to wild type bacteria of the same species.

The genetics of lipid A biosynthesis of enteric bacteria, as it was known at the time of the present invention, is summarized in Schnaitman and Klena (1993*, Microbiol. Rev.* 57:655–682). Genes lpxa, lpxb, lpxC, and lpxD encode gene products which function on the glucosamine backbone of lipid A including transfer of β-hydroxymyristic acid to glucosamine. The htrB gene was described as a gene that affects the inner core structure (KDO, heptose, phosphorylethanolamine (PEA)) which was discovered during a screen for genes necessary for growth of *Escherichia coli* at elevated temperatures. Knockout mutations of htrB resulted in mutant *E. coli* which exhibited a reduced sensitivity to deoxycholate, an inability to grow at temperatures above 32.5° C., and a decrease in LPS staining intensity (Schnaitman et al., 1993, supra; Karow et al., 1992, *J. Bacterial.* 174:7407–7418). Karow et al. further noted that at between about 30° C. to about 42° C., *E. coli* htrB mutants have changes in the fatty acid composition of both LPS and phospholipids, and particularly, overproduce phospholipids, as compared to wild type. However, it was neither known nor suggested which one or more of the at least six molecules of ester- or amide bound fatty acids is lacking in the lipid A portion of LPS of htrB mutants. Also no mention was made that htrB mutants contained a lipid A moiety specifically lacking one or both non-hydroxylated (secondary acyl chain) fatty acids responsible for endotoxicity; i.e. that the htrB mutant contained an altered endotoxin exhibiting reduced in vivo toxicity, but retaining antigenicity ("htrB endotoxin"), as compared to wild type.

The discoveries comprising the present invention include the unexpected results that knockout mutations of the htrB gene of gram-negative bacteria including the family *Enterobacteriaceae*) result in htrB mutants which specifically lack one or more secondary acyl chain fatty acids which are ester-bound to the hydroxyl groups of two of the four molecules of β-OH (as shown in FIG. 2). Thus, it appears that the HtrB protein has either acyltransferase activity, or indirectly or directly affects regulation of acyltransferase activity. The following examples are presented to illustrate preferred embodiments of aspects of the present invention, and are not intended to limit the scope of the invention. In particular, a preferred embodiment is the making of an *H. influenzae* htrB mutant, and methods of using the same as a whole cell, or to isolate therefrom the endotoxin, in vaccine preparations or to generate antibodies for therapeutic or diagnostic applications. However, since the lipid A moiety is highly conserved among bacteria of the family Enterobacteriaceae and closely related gram-negative bacteria, the invention relates to gram-negative bacterial pathogens, as defined previously herein. There is microheterogeneity in terms of the length of the secondary acyl chain (12 or 14 carbon chains) and to which of the four β-OH are substituted (1, 2, or 4) (Erwin et al., 1991*, Infect Immun* 59:1881–1887); however, the nature of the substitution is the same and thus the particular steps (genes and gene products) involved in the biosynthetic pathway appear conserved. For example, removal of secondary acyl chains from various gram-negative bacterial pathogens (*E. coli, H. influenzae, P. aeruginosa, S. typhimurium*, and *N. meningitidis* using human acylxyacyl hydrolase resulted in deacylated LPS from all species tested having significantly reduced mitogenic activity (Erwin et al., 1991, supra) as compared to the respective wild type strain.

EXAMPLE 1

Identification of an htrB Gene, and Generation of htrB Mutants

By complementing a nontypable *H. influenzae* strain 2019 with a *S. typhimurium* rfaE mutant strain, the rfaE gene of *H. influenzae* strain 2019 was cloned (Lee et al., 1995, *Infect Immun* 63:818–824). Sequence analysis of the upstream region of the *H. influenzae* rfaE gene revealed an open reading frame highly homologous to the *E. coli* htrB gene. The *H. influenzae* htrB gene comprises 933 bases and encodes a protein, HtrB, of 311 amino acids (SEQ ID NO:1) and an estimated molecular size of 36 kilodaltons (kDa). Comparison of the deduced amino acid sequence of the *H. influenzae* HtrB with the *E. coli* HtrB revealed shared homology (56% identity and 73% similarity). Cloning the htrB gene of *H. influenzae* into a plasmid, and subsequent in vitro transcription-translation analysis, revealed that HtrB has an apparent molecular size of 32–33 kDa.

There are various standard techniques known to those skilled in the art for mutating a bacterial gene. Those techniques include site-directed mutagenesis, and shuttle mutagenesis using transposons. In one aspect of this embodiment, mutagenesis of the htrB gene was carried out by shuttle mutagenesis. A derivative of the bacterial transposon Tn3, miniTn3 (Seifert et al., 1986, *Proc. Natl. Acad. Sci. USA* 83:735–739), was used as an insertion sequence to mutate the htrB gene. A 2.4 kilobase (kb) BglII containing the htrB gene from *H. influenzae* was cloned into a plasmid which was used as a target for mini-Th3 transposon mutagenesis. Briefly, introduced into a single bacterial cell (*E. coli*), is the plasmid containing the htrB gene; a plasmid immune to Tn3 transposition and containing transposase (which mediates the cointegration between Tn3 and the target molecules); and a plasmid containing mini-Tn3. After allowing for transposition, the bacterial cells are mated with an *E. coli* strain containing the cre enzyme that is used to resolve cointegrates in shuttle mutagenesis. Transconjugates were selected for with antibiotics (kanamycin, ampicillin, and streptomycin) and analyzed by restriction endonuclease digestion.

Two plasmids, termed pB28 and pB29, each with a mini-Tn3 transposon containing the chloramphenicol acetyltransferase (CAT) gene inserted into the htrB open reading frame at a different location. Nontypeable *Haemophilus influenza* strains 2019 B28 and 2019 B29 were deposited on Nov. 14, 2000 with the American Type Culture Collection, 10801 University Blvd., Manassas, Va. 20110-2209 under the provisions of the Budapest Treaty, and all restrictions will be irrevocably removed upon the granting of a patent on this application. Strain B28 has been accorded accession number PTA-2667 and strain B29 has been accorded accession number PTA-2668. Each plasmid was used to transform nontypeable *H. influenzae* strain 2019 and bacterial cell transformants were selected for by growth in the presence of chloramphenicol (1.5 $\mu$g/ml), resulting in identification of mutant strains designated NTHi B28 and B29, respectively. Locations of the mTn3 insertion in the chromosomes of the NTHi mutants were confirmed by genomic Southern hybridization using the 2.4 kb Bg/II fragment as a probe. In particular, a Bg/II digest of NTHi strain 2019 DNA resulted in a 2.4 kb fragment; whereas similar digests of DNA from mutants NTHi B28 and B29 revealed 4.0 kb fragments. Further, the 4.0 kb fragments were digested by EcoRI which is present in the mTn3.

Alternatively, methods are known in the art to perform site-directed mutagenesis into a bacterial gene (See for example, Halladay, 1993, *J. Bacteriol.* 175:624–692), and recombination of the mutated bacterial gene into the bacterial chromosome. A selectable kanamycin resistance cassette may be used to insert into, and mutate, the htrB gene contained within a shuttle plasmid. Subsequent transformation into a bacterial host cell with the shuttle plasmid, and recombination of the bacterial genome (at the site of the genomic copy of the htrB gene) with the cassette via htrB flanking sequences, results in the site-directed mutagenesis of the bacterial htrB gene.

Primer extension analysis can be used to determine the promoter region of the htrB gene. The *H. influenzae* htrB's promoter region was determined by primer extension analysis by first growing the bacteria, harvesting and purifying the RNA, and using a commercial primer extension kit according to the manufacturer's suggestions. A single transcription site was found using a primer (SEQ ID NO:2) complementary to the 5' region of the htrB open reading frame. The first nucleotide was a cytosine (C) residue located at 21 bp upstream of the putative translation start site, ATG. The region upstream of the transcription start site contained a sequence (SEQ ID NO:1, bases 13 to 29) similar to the consensus -10 region of the bacterial $\sigma^{70}$-dependent promoters at an appropriate distance. An element (SEQ ID NO:1, bases 1 to 6) resembles the consensus sequence of the -35 region.

EXAMPLE 2

Characterization of htrB Mutants

Growth Characteristics

NTHi B28 and B29 strains were initially selected at 30° C., and were unable to grow at 37° C. With further passages at 30° C., the NTHi htrB mutants began to lose temperature sensitivity and demonstrated a slow rate of growth, as compared to NTHi 2019, at 37° C. However, for growth temperatures greater than or equal to 38.5° C., the temperature sensitivity remained for the htrB mutants.

It was reported previously that *E. coli* htrB mutants demonstrated a change in membrane permeability to various compounds including kanamycin and deoxycholate (Karow et al., 1992, supra). The NTHi htrB mutants were also tested for sensitivity to kanamycin and deoxycholate. Overnight cultures grown at 30° C. were then diluted and allowed to grow in the presence of 5 $\mu$g/ml kanamycin at either 30° C. or 37° C. At 30° C., no difference was detected in the growth rate between NTHi 2019 and the NTHi htrB mutant strains in the absence of kanamycin. However, the growth of the htrB mutants was significantly inhibited in the presence of kanamycin, whereas NTHi 2019 was not affected. For the htrB mutants, the sensitivity to kanamycin was even greater at 37° C., since the mutants failed to show growth in the presence of kanamycin at 37° C. Likewise, at 30° C. the htrB mutants showed sensitivity, as compared to NTHi strain 2019, at concentrations of greater than 500 $\mu$g/ml deoxycholate, and failed to grow at 1000 $\mu$g/ml. At 37° C., the htrB mutants showed almost complete inhibition of growth in the presence of only 250 $\mu$g/ml deoxycholate.

Endotoxin Characteristics

The LPS of *E. coli* htrB mutants has been characterized as being weakly stained on silver-stained polyacrylamide gels, but its migration pattern did not vary as compared to LPS from wild type. In contrast, the LOS from NTHi mutants B28 and B29 migrated faster than that from NTHi strain 2019 on silver-stained gels. Additionally, the LOS from the mutants displayed a brownish color rather than black, as displayed by NTHi 2019. Reconstitution, by introducing a plasmid with an intact htrB gene into the mutant, of NTHi mutant B29 confirmed that the differences in growth characteristics and LOS migration and staining were due to mutation of the htrB gene.

The htrB mutant LOS and wild type LOS were each analyzed by electrospray ionization-mass spectrometry (ESI-MS) to provide molecular mass profiles for the different components of LOS. First, LOS was isolated from the respective strains. LPS or LOS can be isolated by the phenol-water method (Westphal et al., 1965, *Methods in Carbohydrate Chemistry* 5:83–91); or using an alternative purification procedure (using a protease; Hitchcock et al., 1983, *J. Bacteriol.* 154:269–277). The isolated LOS species were then O-deacylated by mild hydrazine treatment (37° C. for 20 minutes; see Phillips et al., 1990, *Biomed. Environ. Mass Spectrom.* 19:731–745). Analysis by ESI-MS of the different LOS species showed that while the O-deacylated LOS from NtHi mutant B29 and NTHi 2019 were similar in molecular mass profile, two differences can be clearly discerned. In the htrB mutant, there is a decrease (50% reduction) in the amount of LOS containing two phosphoethanolamines (PEA) in the inner core structure; and there is a shift to high molecular weight LOS species containing more hexoses. These findings suggest that the degree of phosphorylation may be affecting chain progression from specific heptose moieties, and that HtrB either directly or indirectly affects phosphorylation of LOS.

Mass spectrometry was used to analyze the lipid A. More specifically, lipid A from htrB mutant LOS and from wild type LOS were each analyzed by liquid secondary ion mass spectrometry (LSIMS) in the negative ion mode to provide a spectrum of molecular ions for the different components lipid A. First, the LOS species were each hydrolyzed in 1% acetic acid for 2 hours at 100° C. at a concentration of 2 mg/ml. The hydrolysates were centrifuged, and the supernatants removed. The water soluble crude lipid A fractions were washed twice in water, and once in an organic mixture (chloroform/methanol/water; by volume 2:1:1) and then evaporated to dryness. For analysis, the lipid samples were redissolved in $CH_2Cl_2/CH_3OH$ (3:1, v/v) and 1 μl of nitrobenzylalcohol/triethanolamine (1:1, v/v) and applied as a liquid matrix onto a mass spectrometer. LSIMS of the wild type (NTHi 2019) revealed a spectrum containing two deprotonated molecular ions consistent with a hexaacyl lipid A structure containing either one (hexaacyl monophosphoryl lipid A, $M_T=1744$) or two phosphates (hexaacyl diphosphoryl lipid A, $M_T=1824$). This spectrum is essentially identical to that reported for the lipid A structure of LOS of *H. ducreyi* (Melaugh et al., 1992, *J. Biol. Chem.* 267:13434–13439). The lower mass fragments are believed to be ions which arise through LSIMS-induced fragmentation of higher mass mono- and diphosphorylated molecular ion species.

Figure 2A:
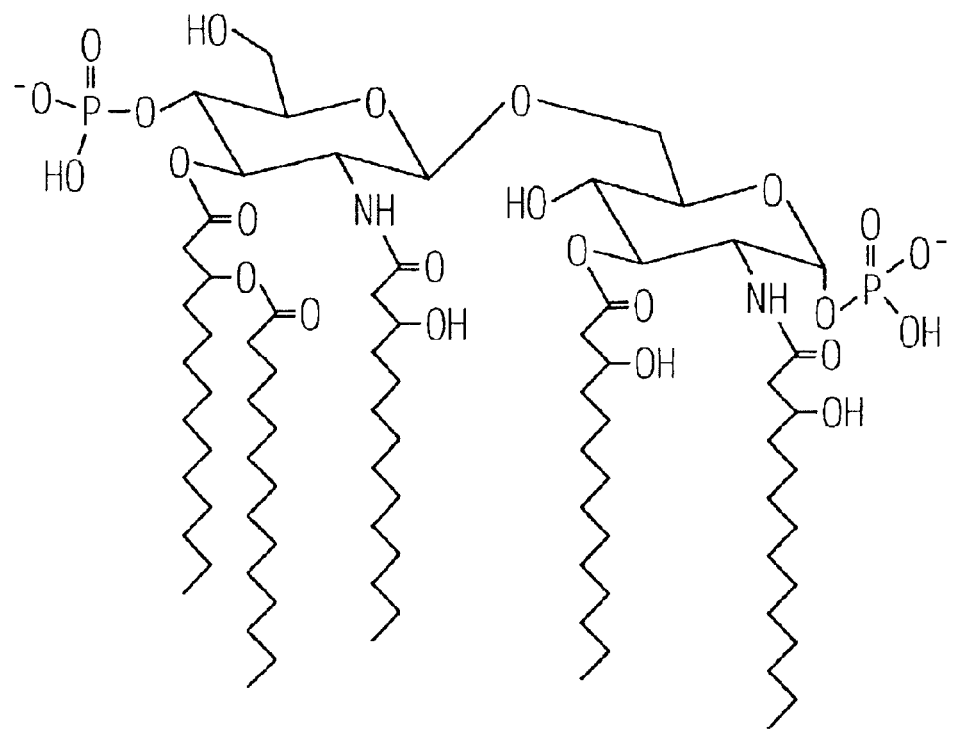
FIG. 2A is a schematic representation of the general structure of a species of lipid A, from the LOS of an htrB mutant comprising pentaacyl diphosporyl lipid A.
Figure 2A:
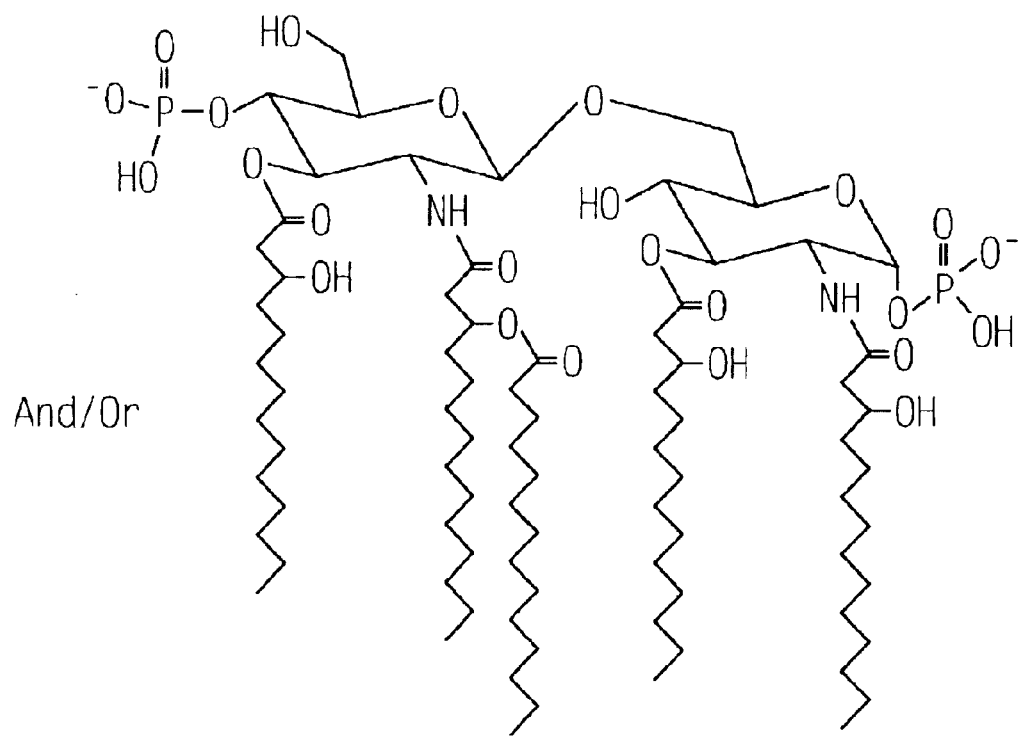
Figure 2B:
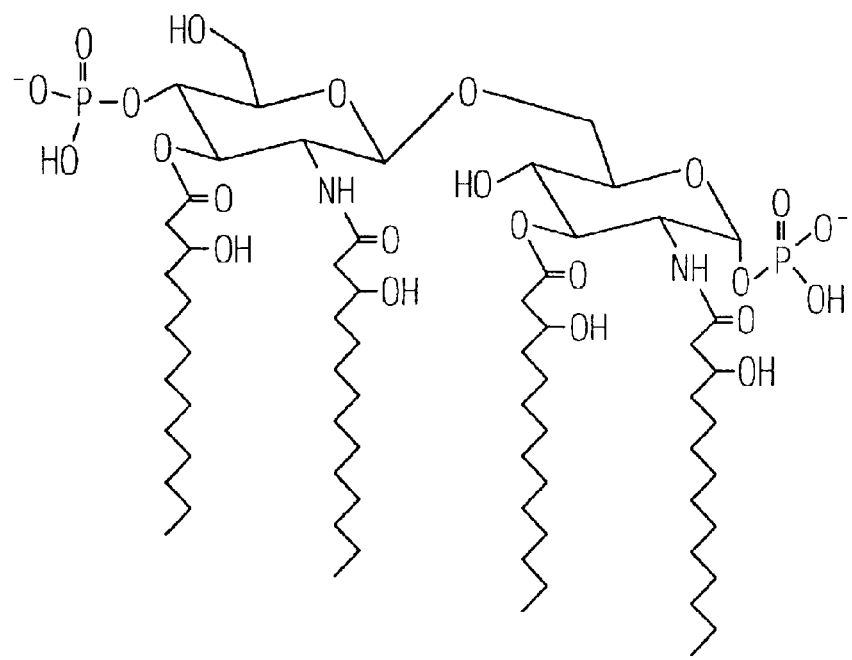
FIG. 2B is a schematic representation of the general structure of a species of lipid A, from the LOS of an htrB mutant, comprising tetraacyl diphosporyl lipid A.

In contrast, the LSIMS spectrum for the lipid A preparation from the htrB mutant-LOS lacks molecular ions corresponding to the wild type hexaacyl lipid A species. There are two high mass ions which correspond to the molecular ions for a mono- and diphosphoryl pentacyl lipid A species missing one of the secondary acyl chains (e.g. myrisitic acid moiety). Further, at the lower masses are two additional molecular ion species that correspond to a mono- and diphosphoryl tetraacyl lipid A species lacking both secondary acyl chains. In summary, the lipid A structure of the wild type's LOS is hexaacyl; whereas the lipid A structure of the htrB mutant shows two species, a tetraacyl (FIG. 2A) and a pentaacyl species (FIG. 2B) indicating the loss of at least one, and sometimes both secondary acyl chains.

EXAMPLE 3

Substantially Reduced Toxicity of htrB Mutants

The effect due to the lack of one or more secondary acyl chains on the toxicity of a gram-negative bacterial pathogen was examined using a standard in vitro assay for measuring in vivo toxicity. Murine macrophage-like cell line J774, when stimulated by LPS, secretes TNFα. The amount of TNFα, a directly proportional to the toxicity of the stimulating LPS, can be measured by (a) removing the cell-free supernatant containing the TNFα; (b) adding the supernatant to a TNFα-sensitive cell line, such as WEHI 164; and (c) measuring the resultant cytotoxicity (See for example, Espevik et al., 1986, *J Immunol Methods* 95:99; Sakurai et al., 1985, *Cancer Immunol Immunother* 20:6–10; Adams et al., 1990, *J Clin Microbiol* 28:998–1001; Adams et al., 1990, *J Leukoc Biol* 48:549–56; Tsai et al., 1992, *Cell Immunol* 144:203–16; and Pfister et al., 1992, *Immunol* 77:473–6).

In this assay, adherent J774 cells were removed from culture, washed with PBS-1 mM EDTA, and then washed twice with complete tissue culture medium without antibiotics. $2 \times 10^6$ to $4 \times 10^6$ J774 cells/100 mm culture dish were incubated in tissue culture medium overnight in a $CO_2$ incubator. Adherent J774 cells are removed with PBS-1 mM EDTA, washed three times in tissue culture medium, and adjusted to $5 \times 10^5$/ml. Aliquots of 50 μl were added per well of a round bottom 96 well plate. The plate is then incubated for 1 hour at 37° C. in a $CO_2$ incubator. Per well is added either an htrB mutant, or the wild type strain, in various colony forming units (cfu, infection dose). The plate is then incubated at 37° C. for 1 hour in a $CO_2$ incubator. After the incubation, 100 μl of culture medium containing 50 μg/ml gentamycin is added per well. The plate is then incubated overnight at 37° C. in a $CO_2$ incubator. Aliquots of S01 of the J774 supernatant were removed per well and transferred into wells of a flat bottom 96 well plate. Serial 10 fold dilutions were made of the J774 supernatant. Included as a control is a dilution series of recombinant TNFα (rTNFα). Added per well is 50 μl of WEHI 164 clone 13 cells at $6 \times 10^5$ cells/ml in tissue culture medium+25 mM LiCl+2 μg/ml actinomycin D; and the mixture was incubated overnight at 37° C. in a $CO_2$ incubator. After the incubation, 10 μl of alomar blue is added, and 5–7 hours later the optical density is read at 570 nm. The assay utilizes alomar blue as a color indicator; i.e., alomar blue is converted to a red color by living cells, but remains blue if the cells are killed.

Figure 3:
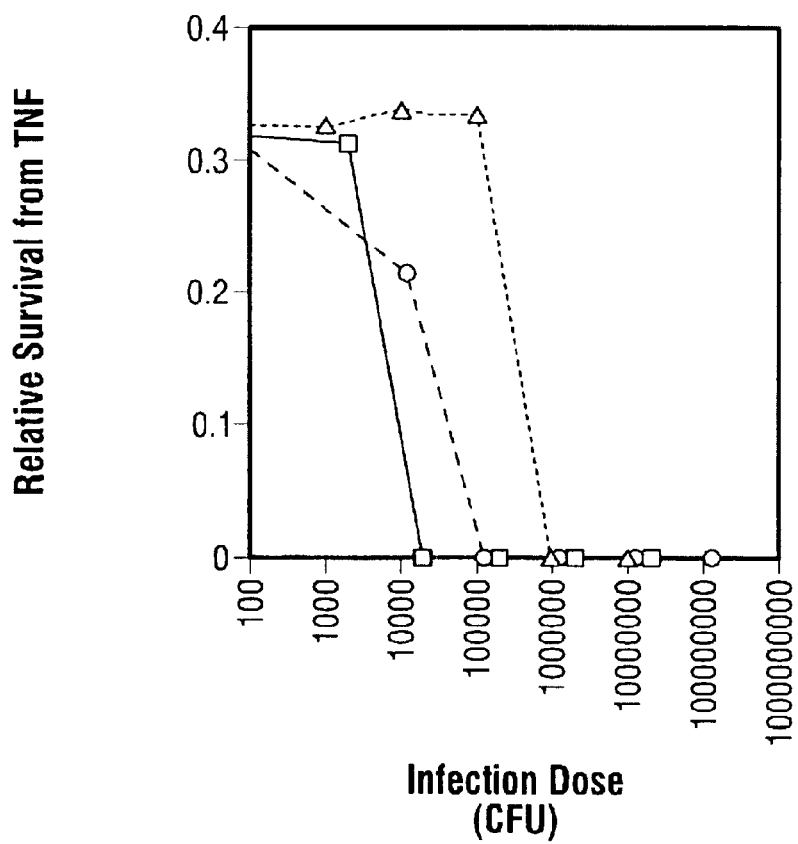
FIG. 3 is a graph showing the relative toxicity of an htrB mutant (○, △) as compared to wild type bacteria (□) in a TNFα release assay.

FIG. 3 shows a comparison between the number of bacterial cells of *H. influenzae* strain 2019 (wild type, □), and of bacterial cells of htrB mutant NTHi B29 (○ and Δ) necessary to stimulate the release of enough TNFα from J774 cells to kill the TNFα-susceptible cell line WEHI 164. $B29_{hi}$ (Δ) and $B29_{LO}$ (○) refer to a high number and low number of passages of htrB mutant, respectively. As shown in FIG. 3, the htrB mutant shows a reduced ability to stimulate TNFα release; i.e., between an approximately 10 fold reduction ($B29_{LO}$) to an approximately 100 fold reduction ($B29_{hi}$). This reduced ability to stimulate TNFα is one indication of the htrB mutant being substantially reduced in toxicity due to the lack of one or more secondary acyl chains in the lipid A porton of the endotoxin.

The substantial reduction in toxicity exhibited by the htrB mutant, as observed by the TNFα release assay, due to the lack of one or more secondary acyl chains is further supported by previously reported assays of bioactivity of endotoxin treated with acyloxyacyl hydrolase which selectively removes the secondary acyl chains from endotoxin. Deacylated endotoxin from *E. coli, H. influenzae, N. meningitidis,* and *S. typhimurium* were (a) similarly reduced in potency in the *Limulus* lysate test relative to the respective wild type endotoxin; (b) reduced in the ability to stimulate neutrophil adherence to human endothelial cells relative to the respective wild type endotoxin; and (c) reduced in mitogenic activity for murine splenocytes (Erwin et al., 1991, *Infect Immun* 59:1881–1887); yet maintained expression of antigenic epitopes. Similarly, *S. typhimurium* LPS treated with acyloxacyl hydrolase showed a reduction in toxicity by 100-fold or greater in a dermal Shwartzman reaction; was less pyrogenic in a thermal response model; showed a 5 to 12 fold reduction in B-cell mitogenicity; and showed a 10 to 20 fold reduction in the release of prostaglandin $E_2$, as compared to wild type endotoxin, in concluding that maximally deacylated LPS was at least 10 fold less toxic than wild type endotoxin (U.S. Pat. No. 4,929,604).

EXAMPLE 4

Use of htrB Mutants as Immunogens

In one aspect of this embodiment, the htrB mutant is used as a whole cell vaccine. The benefit of using live, attenuated (weakened in its ability to cause pathogenesis) bacteria as an immunogen in a vaccine formula is that they are able to survive and may persist in the human or animal body, and thus confer prolonged immunity against disease. In conjunction with the benefit of using a live bacteria to prolong the immune response, gram-negative bacterial pathogens which are htrB mutants have the added benefit in that they exhibit substantially reduced toxicity. Another advantage, as compared to a vaccine formulation comprising an isolated peptide representing a bacterial antigen, is that a bacterial antigen expressed on the surface of a bacterial cell will often result in greater stimulation of the immune response. This is because the surface of bacteria of the family Enterobacteriaceae acts as a natural adjuvant to enhance the immune response to an antigen presented thereon (Wezler, 1994, *Ann NY Acad Sci* 730:367–370). Thus, using a live bacterial vaccine, such as an htrB mutant, to express complete proteins in an native conformation (i.e., as part of the bacterial outer membrane) is likely to elicit more of a protective immune response than an isolated protein alone.

Live bacterial vaccine vectors of the family Enterobacteriaceae that have been described previously include attenuated *Salmonella* strains (Stocker et al., U.S. Pat. Nos. 5,210,035; 4,837,151; and 4,735,801; and Curtiss et al., 1988, Vaccine 6:155–160; herein incorporated by reference), and *Shigella flexneri* (Sizemore et al., 1995, *Science* 270:299–302; herein incorporated by reference). One preferred embodiment is to provide a vaccine delivery system for human or animal (depending on the genus and species of the gram-negative bacterial pathogen) mucosal pathogens. Thus, immunization by the parental route or by the mucosal route with a prophylactically effective amount of the htrB mutant, or an htrB mutant transformed to recombinantly express additional bacterial antigens (that do not negatively affect the growth or replication of the transformed htrB mutant), can lead to colonization of mucosal surfaces to induce mucosal immunity against the antigens displayed on the surface of, or secreted from the htrB mutant. The resultant htrB mutant can be used in a vaccine formulation which expresses the bacterial antigen(s).

Similar methods can be used to construct an inactivated htrB mutant vaccine formulation except that the htrB mutant is inactivated, such as by chemical means known in the art, prior to use as an immunogen and without substantially affecting the immunogenicity of the expressed immunogen (s). For example, human bronchial mucosal immunity has been stimulated with an aerosol vaccine comprising lysed *H. influenzae* (Latil et al., 1986, *J Clin Microbiol* 23:1015–1021). Either of the live htrB mutant vaccine or the inactivated htrB mutant vaccine may also be formulated with a suitable adjuvant in order to further enhance the immunological response to the antigen(s) expressed by the vaccine vector, as to be described in more detail.

In another aspect of this embodiment, the endotoxin is isolated from the htrB mutant using methods known in the art, and the isolated htrB endotoxin is used in a vaccine formulation. As mentioned previously, major antigenic determinants of gram-negative bacteria are believed to reside in the carbohydrate structure of the O-specific side chain of LPS and the complex carbohydrate structure of LOS. However, the chemical nature of LPS and LOS prevent the use of these molecules in vaccine formulations; i.e., active immunization with LPS or LOS is unacceptable due to the inherent toxicity of the secondary acyl chains of the lipid A portion of endotoxin. The endotoxin isolated from an htrB mutant of a gram-negative bacterial pathogen lacks one or more secondary acyl chains, and thus exhibits substantially reduced toxicity as compared to endotoxin isolated from the respective wild type bacteria. Therefore, endotoxin isolated from an htrB mutant of a gram-negative bacterial pathogen can be used in a vaccine formulation in inducing immunity against the respective wild type gram-negative bacterial pathogen. LPS or LOS can be isolated by the phenol-water method (Westphal et al., 1965, *Methods in Carbohydrate Chemistry* 5:83–91); or using an alternative purification procedure (using a protease; Hitchcock et al., 1983, *J. Bacterial.* 154:269–277).

Many methods are known for the introduction of a vaccine formulation into the human or animal (collectively referred to as "individual") to be vaccinated. These include, but are not limited to, intradermal, intramuscular, intraperitoneal, intravenous, subcutaneous, ocular, intranasal, and oral administration. Conventionally, vaccine formulations containing either live bacteria, or attenuated or inactivated bacteria, are administered by injection or by oral administration. For example, respiratory immunity can be stimulated by intestinal immunization with purified *H. influenzae* antigens (Cripps et al., 1992, *J. Infect Dis* 165S1:S199–201; herein incorporated by reference). The vaccine formulation may comprise a physiologically acceptable solution as a carrier in which the htrB bacterial cells or isolated htrB endotoxin is suspended. Various adjuvants may be used in conjunction with vaccine formulations. The adjuvants aid by modulating the immune response and in attaining a more durable and higher level of immunity using smaller amounts of vaccine antigen or fewer doses than if the vaccine antigen were administered alone. Examples of adjuvants include incomplete Freund's adjuvant, Adjuvant 65 (containing peanut oil, mannide monooleate and aluminum monostearate), oil emulsions, Ribi adjuvant, the pluronic polyols, polyamines, Avridine, Quil A, saponin, MPL, QS-21, and mineral gels such as aluminum hydroxide, aluminum phosphate, etc. The vaccine formulation is administered in a prophylactically effective amount to be immunogenic, which depends on factors including the individual's ability to mount an immune response, the degree of protection to be induced, and the route of administration.

In another aspect of the invention, the vaccine formulation can be administered orally by including it as part of the feed given to economically important livestock. As known by those skilled in the art, species of *Haemophilus*, *Campylobacter*, *Pseudomonas*, and *Salmonella* are pathogenic for economically important livestock. Using the methods according to the present invention, as illustrated in the following examples, htrB mutants of such animal pathogens can be produced. The resultant htrB mutants, or endotoxin isolated therefrom, can be used in a vaccine formulation. Use of vaccine formulations, containing one or more antigens of various microbial pathogens, in animal feed has been described previously (See for example, Pritchard et al., 1978, *Avian Dis* 22:562–575).

EXAMPLE 5

*H. influenzae* htrB Mutants as Immunogens

In one embodiment, the htrB mutant is an *H. influenzae* htrB mutant. *Haemophilus influenzae* is an important human respiratory tract pathogen in diseases including otitis media, chronic sinusitis, and chronic obstructive pulmonary disease. Certain surface-exposed bacterial components, including P2, P6, and LOS, appear to be antigens which may confer a protective immune response in immunized humans. Such antigens have been shown to be targets of bactericidal antibody, and the presence of serum bactericidal antibody is associated with protection from infection by *H. influenzae* (Faden et al., 1989; *J. Infect. Dis.* 160:999–1004).

In one aspect of this embodiment the *H. influenzae* htrB mutant is genetically engineered to express one or more heterologous bacterial antigens. As will be discussed in more detail below, *H. influenzae* has a natural genetic transformation process involving linearized DNA binding, uptake via one or more uptake sequences (e.g. AAGTGCGGT-SEQ ID NO:3), translocation, and recombination. Thus, one mechanism to introduce a recombinant DNA molecule containing the at least one heterologous bacterial antigen to be expressed, is to transform the host *H. influenzae* htrB mutant with linearized recombinant DNA molecule containing the DNA encoding the at least one heterologous bacterial antigen ("the encoding sequence"). Alternatively, the recombinant DNA molecule containing the encoding sequence to be expressed can be inserted into a plasmid vector, and either introduced into as a linearized recombinant molecule by the natural transformation process; as circularized recombinant plasmid using electroporation of noncompetent *H. influenzae* htrB mutants; or as a circularized recombinant plasmid transformed into competent *H. influenzae* htrB mutants.

Plasmids useful for cloning of and expression from recombinant DNA molecules in *H. influenzae* are known to those skilled in the art. Such plasmids include:

pRSF0885 confers ampicillin resistance, and contains a PvuII cloning site and a defective TnA sequence (Setlow et al., 1981, *J. Bacteriol.* 148:804–811), and can replicate in both *H. influenzae* and *E. coli* (Trieu et al., 1990, *Gene* 86:99–102).

pDM2 was constructed by cloning chloramphenicol resistance into pRSF0885; and pDM5 was constructed by cloning tetracycline resistance into pRSF0885 (McCarthy et al., 1986, *J. Bacteriol.* 168:186–191).

pVT63, pVT64, pVT65, pVT66 are improved shuttle vectors for *H. influenzae* and *E. coli* based on pDM2 (Trieu et al., 1990, *Gene* 86:99–102), and contain the pUC-derivative of the ColE1 ori, and the pRSF0885 rep locus. Additionally, each plasmid has drug markers with unique restriction sites for insertional inactivation of the drug marker as follows: pVT63-ApR (HincII, PstI, ScaI), KmR (ClaI, HindIII, NruI, SmaI, XhoI); pVT64-ApR (HincII, PstI, ScaI, SspI), SpR; pVT65-ApR (HincII, PstI, ScaI, PvuI, SspI), CmR (BalI, NcoI); pVT66-ApR (HincII, PstI, ScaI, PvuI), CmR (SmaI).

pACYC177, pACYC184, pSU2718, pSU2719 are improved shuttle vectors for *H. influenzae* and *E. coli* based on p15A (Chandler, 1991, *Plasmid* 25:221–224), have the p15A ori, and were compatible with a plasmid containing the RSF0885 origin of replication. Additionally, each plasmid has multiple cloning sites restriction sites and drug markers as follows: pACYC177-ApR, KmR (Accession No. X06402); pACYC184-CmR, TcR (Accession No. X06403); pSU2718 CmR and polycloning site from pUC18 (Accession No. M64731); and pSU2719-CmR and polycloning site from pUC19 (Accession No.M64732).

pQL1 is an improved shuttle vector for use in *H. influenzae* and *E. coli* containing both the pMB1 ori and P15a ori, KmR which is flanked by *H. influenzae* uptake sequences, a multiple cloning site containing a unique BamHI and SmaI restriction sites, and which is particularly suited for analyzing *H. influenzae* promoter strength in *H. influenzae* (Heidecker et al., 1994, *Gene* 150:141–144).

In cloning the recombinant DNA molecule containing the encoding sequence into a plasmid vector, one skilled in the art will appreciate that the choice of restriction enzymes for digesting both the recombinant DNA molecule and the plasmid to result in compatible ends for ligation depends on the unique restriction enzyme sites at the ends of the recombinant DNA molecule, whether occurring naturally or engineered such as during enzymatic amplification; one or more unique restriction enzyme sites within the plasmid vector; whether insertion into the plasmid vector will assist in the selection process (See, e.g., pVT66); and whether a plasmid-derived promoter is used solely, or in addition to the promoter(s) of the encoding sequences, to drive expression from the recombinant DNA molecule. Selection and screening of transformed *H. influenzae* htrB mutants may be accomplished by methods known in the art including detecting the expression of a marker gene (e.g., drug resistance marker) present in the plasmid, and immunodetection of the expressed and displayed heterologous bacterial antigen. While this aspect of the embodiment illustrates that the recombinant DNA molecule containing the encoding sequence can be inserted into a plasmid and expressed in *H. influenzae* htrB mutants, it will be appreciated by those skilled in the art that vectors other than plasmids, can be used including, but not limited to, bacteriophage vectors.

Successful expression of the at least one heterologous bacterial antigen requires that either the recombinant DNA molecule comprising the encoding sequence, or the vector itself, contain the necessary control elements for transcription and translation which is compatible with, and recognized by the particular host system used for expression. Using methods known in the art of molecular biology, including methods described above, various promoters and enhancers can be incorporated into the vector or the recombinant DNA molecule containing the encoding sequence to increase the expression of the heterologous bacterial antigen, provided that the increased expression of the heterologous bacterial antigen(s) is compatible with (for example, non-toxic to) the htrB mutant. As referred to herein, the encoding sequence can contain DNA encoding more than one heterologous bacterial antigen, and may include viral and/or fungal antigen-encoding sequences, to create a multivalent antigen for use as an improved vaccine composition.

The selection of the promoter will depend on the expression system used. For example, a preferred promoter in an *H. influenzae* expression system may be the P2 or P6 promoter operatively linked to the encoding sequence. Promoters vary in strength, i.e. ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising *E. coli* include the lac promoter, trp promoter, recA promoter, ribosomal RNA promoter, the $P_R$ and $P_L$ promoters, lacUV5, ompF, bla, lpp, and the like, may be used to provide transcription of the inserted encoding sequence.

Other control elements for efficient gene transcription or message translation include enhancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the encoding sequence to increase transcriptional efficiency. These or other regulatory sites, such as transcription or translation initiation signals, can be used to regulate the expression of the encoding sequence. Such regulatory elements may be inserted into the recombinant DNA molecule containing the encoding sequence, or nearby vector DNA sequences using recombinant DNA methods described herein, and known to those skilled in the art, for insertion of DNA sequences.

Accordingly, a recombinant DNA molecule containing an encoding sequence, can be ligated into an expression vector at a specific site in relation to the vector's promoter, control, and regulatory elements so that when the recombinant vector is introduced into the htrB mutant, the heterologous bacterial antigen can be expressed in the host cell. The recombinant vector is then introduced into the htrB mutant, and the transformed htrB mutants are selected, and screened for those cells containing the recombinant vector. Selection and screening may be accomplished by methods known in the art, and depending on the vector and expression system used.

The introduction of a recombinant DNA molecule containing the encoding sequence (including an expression vector or plasmid containing the same) into *H. influenzae* htrB mutants can be accomplished in any one of three processes: a natural genetic transformation process; transformation of competent bacterial cells; and electroporation of non-competent bacterial cells.

Natural Transformation Process

The natural genetic transformation process of *H. influenzae* involves linearized DNA binding, uptake via one or more uptake sequences, translocation, and recombination. Thus, one mechanism to introduce a recombinant DNA molecule containing the encoding sequence to be expressed into at least one heterologous bacterial antigen, is to transform the host *H. influenzae* with linearized recombinant DNA molecule containing the encoding sequence; or a linearized vector having inserted into it the recombinant DNA molecule containing the encoding sequence to be expressed. In this natural process, when the linearized DNA is translocated intracellularly, one of the translocated strands of DNA is apparently degraded by exonuclease activity (Barany et al., 1983, *Proc. Natl. Acad. Sci. USA* 80:7274–7278). If the translocated strand lacks homology sufficient for recombination into the *H. influenzae* chromosome, the translocated strand becomes susceptible to further degradation (Pifer et al., 1985, *Proc. Natl. Acad. Sci. USA* 82:3731–3735). Using methods known in the art (e.g., Barany et al., 1983, supra; herein incorporated by reference), linearized DNA containing the encoding sequence can be introduced into *H. influenzae* htrB mutants. Since the encoding sequence can be flanked by *H. influenzae* sequences, to increase the likelihood of recombination of the encoding sequence into the *H. influenzae* htrB mutants' genome is likely to occur.

Transformation of Competent Bacterial Cells

Another mechanism to introduce a recombinant DNA molecule containing the encoding sequence to be expressed into at least one heterologous bacterial antigen, is to transform competent host *H. influenzae* htrB mutants with a circular vector, such as a plasmid, having inserted into it the recombinant DNA molecule containing the encoding sequence to be expressed. Competence of *H. influenzae* develops best under conditions in which the bacterial cell duplication is inhibited, such as a temporary shift to anaerobic conditions, by physiological change occurring during late-log phase growth, and transfer of cells into nutrient-poor, chemically-defined medium. Such defined media for the development of competence of *H. influenzae* has been previously described in detail (Herriott et al., 1970, *J. Bacteriol.* 101:517–524; herein incorporated by reference). It appears that only a short time after entering competent *H.influenzae*, a plasmid containing sequences homologous to the bacterial chromosome can insert its homologous sequence (such as the encoding sequence flanked by *H. influenzae* sequences) into the chromosome via recombination (Setlow et al., 1981, supra). for expression. Thus, in this embodiment, a plasmid containing the encoding sequence which is capable of being transformed into competent *H. influenzae* htrB mutants is introduced by methods for transformation known in the art (Karudapuram et al., 1995, *J. Bacteriol.* 177:3235–3240; Setlow et al., 1981, supra, herein incorporated by reference). The encoding sequence may then be recombined into the *H. influenzae* htrB mutants' genome where it is expressed under the control of its own promoter or an *H. influenzae* promoter near the site of insertion. Such transformation is reported to be at a relatively high frequency (McCarthy and Cox, 1986, *J. Bacteriol.*, 168:186–191).

Alternatively, transformation of competent *H. influenzae* htrB mutants by a circular plasmid with the appropriate origin(s) of replication and containing the encoding sequence may result in plasmid establishment; i.e., a plasmid coexisting as an extrachromosomal element without recombination. Examples of such plasmids have been described above. Thus, in this variation of the embodiment, a plasmid containing the encoding sequence which is capable of being transformed into, and established in, competent *H. influenzae* htrB mutants is introduced by methods for transformation known in the art. The encoding sequence is then expressed from the plasmid under the control of its own promoter or a promoter within the vector.

Electroporation of Non-Competent Bacterial Cells

Yet another mechanism to introduce a recombinant DNA molecule containing the encoding sequence to be expressed into at least one heterologous bacterial antigens, is to introduce a circular vector, such as a plasmid having inserted into it the recombinant DNA molecule containing the encoding sequence to be expressed, into non-competent host *H. influenzae* htrB mutants by electroporation. Electroporation has been used to efficiently introduce plasmid DNA into bacteria. However, optimal conditions may differ depending on the host cell used. Optimal conditions have been described for electroporating plasmid DNA into *H. influenzae* (Mitchell et al., 1991, *Nucl. Acids Res.* 19:3625–3628; herein incorporated by reference). It was found that electroporation of plasmid into *H. influenzae* made competent by defined, nutrient poor media was several orders of magnitude less efficient than electroporation into non-competent *H. influenzae*. Thus, in this variation of the embodiment, it would be preferred that a plasmid containing the encoding sequence is electroporated into non-competent *H. influenzae* htrB mutants. The plasmid is capable of being established in *H. influenzae* htrB mutants, or is degraded after the encoding sequence has recombined into the *H. influenzae* htrB mutants' genome. In either case, the encoding sequence is under the control of its own promoter; or a promoter within the vector or genome, respectively.

EXAMPLE 6

*Neisserial* htrB Mutants as Immunogens

In another embodiment, the htrB mutant is a *Neisserial* htrB mutant selected from the group including *Neisseria* gonorrhoeae, and *Neisseria meningitidis*. *N. gonorrhoeae* is a gram-negative bacterial pathogen causing the sexually transmitted disease gonorrhea, which subsequently can lead to pelvic inflammatory disease in females. *N. meningitidis* is a gram-negative bacterial pathogen which can cause a variety of clinical infections including bacteremia, septicemia, meningitis, and pneumonia. Alterations in the terminal glycosylation of the LOS of *Neisseria* are believed correlate with serum sensitivity and serum resistance of the organism. Further, protective bactericidal antibody is directed against type-specific antigens of *N. meningitidis*, wherein the type-specific antigens have been identified as outer membrane proteins, or LOS, or both.

Using the methods according to the present invention, as illustrated in Examples 1–3, htrB mutants of a *Neisserial* species can be produced and identified. One skilled in the art, using the htrB gene of *H. influenzae*, can isolate the htrB gene of the *Neisserial* species, and produce a mutated htrB gene (unable to encode functional HtrB) using transposon mutagenesis with subsequent recombination resulting in a *Neisserial* htrB mutant lacking one or more secondary acyl chains. Alternatively, there may be sufficient homology between *Neisseria* and *Haemophilus* to use plasmids pB28 and pB29, each with a mini-Tn3 transposon containing the chloramphenicol acetyltransferase (CAT) gene inserted into the htrB open reading frame at a different location, to transform the *Neisserial* species for recombination of the mutant htrB gene into the *Neisserial* htrB gene. *Neisserial* transformants are then selected for by growth in the presence of chloramphenicol (1.5 µg/ml), resulting in identification of *Neisserial* htrB mutant strains. Locations of the mTn3 insertion in the chromosomes of the *Neisserial* htrB mutants may be confirmed by genomic Southern hybridization using a probe containing htrB sequences. The resultant *Neisserial* htrB mutants can then be tested for substantially reduced toxicity using assays described by those skilled in the art for measuring the toxic effects induced by endotoxin.

Using the methods according to the present invention, as illustrated in Examples 4 & 5, *Neisserial* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *Neisserial* species are known to those skilled in the art, including:

pLES2 confers ampicillin resistance, is a shuttle vector functional in both *E. coli* and *N. gonorrhoeae*, and contains a polylinker with restriction sites for EcoRI, SmaI, and BamHI (Stein et al., 1983, *Gene* 25:241–247).

*Neisserial* species also contain a natural transformation process (Rudel et al., 1995, *Proc Natl Acad Sci USA* 92:7896–90; Goodman et al., 1991, *J Bacteriol* 173:5921–5923); and can also be made competent or be electroporated using techniques known to those skilled in the art.

EXAMPLE 7

*Haemophilus ducreyi* htrB Mutants as Immunogens

In another embodiment, the mutant is a *H. ducreyi* htrB mutant. *H. ducreyi* is a gram-negative bacterial pathogen causing a genital ulcer disease, chancroid. Using the methods according to the present invention, as illustrated in Examples 1–3, *H. ducreyi* htrB mutants can be produced and identified. One skilled in the art, using the htrB gene of *H. influenzae*, can isolate the htrB gene of *H. ducreyi*, and produce a mutated htrB gene (unable to encode functional HtrB) using transposon mutagenesis with subsequent recombination resulting in an *H. ducreyi* htrB mutant lacking one or more secondary acyl chains. Alternatively, there is likely sufficient homology between *H. ducreyi* and *H. influenzae* to use plasmids pB28 and pB29, each with a mini-Tn3 transposon containing the chloramphenicol acetyltransferase (CAT) gene inserted into the htrB open reading frame at a different location, to transform H. ducreyi for recombination of the mutant htrB gene into the *H. ducreyi* htrB gene. *H. ducreyi* transformants are then selected for by growth in the presence of chloramphenicol (1.5 µg/ml), resulting in identification of *H. ducreyi* htrB mutant strains. Locations of the mTn3 insertion in the chromosomes of the *H. ducreyi* htrB mutants may be confirmed by genomic Southern hybridization using a probe containing htrB sequences. The resultant *H. ducreyi* htrB mutants can then be tested for substantially reduced toxicity using assays described by those skilled in the art for measuring the toxic effects induced by endotoxin.

Using the methods according to the present invention, as illustrated in Examples 4 & 5, *H. ducreyi* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *Haemophilus* species are known to those skilled in the art, as disclosed in Example 5; and can also be made competent or be electroporated using techniques known to those skilled in the art, as disclosed in Example 5.

EXAMPLE 8

*Campylobacter jejuni* htrB Mutants as Immunogens

In another embodiment, the mutant is a *C. jejuni* htrB mutant. *Campylobacter jejuni* is a gram-negative bacterial pathogen causing human enteritis. Infection by *C. jejuni* has also been associated with the onset of neurologic disorders such as Guillian-Barrè syndrome. *C. jejuni* htrB mutants can be produced and identified. One skilled in the art, using the htrB gene of *H. influenzae*, can isolate the htrB gene of *C. jejuni*, and produce a mutated htrB gene (unable to encode functional HtrB) using transposon mutagenesis with subsequent recombination resulting in an *C. jejuni* htrB mutant lacking one or more secondary acyl chains. Alternatively, there may be sufficient homology between *C. jejuni* and *H. influenzae* to use plasmids pB28 and pB29, each with a mini-Tn3 transposon containing the chloramphenicol acetyltransferase (CAT) gene inserted into the htrB open reading frame at a different location, to transform *C. jejuni* for recombination of the mutant htrB gene into the *C. jejuni* htrB gene. *C. jejuni* transformants are then selected for by growth in the presence of chloramphenicol (1.5 µg/ml), resulting in identification of *C. jejuni* htrB mutant strains. Locations of the mTn3 insertion in the chromosomes of the *C. jejuni* htrB mutants may be confirmed by genomic Southern hybridization using a probe containing htrB sequences. The resultant *C. jejuni* htrB mutants can then be tested for substantially reduced toxicity using assays described by those skilled in the art for measuring the toxic effects induced by endotoxin.

Using the methods according to the present invention, as illustrated in Examples 4 & 5, *C. jejuni* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *C. jejuni* are known to those skilled in the art, and includes:

pUA466 confers tetracycline resistance, and contains an unique AvaI site and AvaII site (Taylor, 1986, *J Bacteriol* 165:1037–39). *C. jejuni* can also be made competent or be electroporated using techniques known to those skilled in the art.

EXAMPLE 9

*Moraxella catarrhalis* htrB Mutants as Immunogens

In another embodiment, the mutant is a *M. catarrhalis* htrB mutant. *Moraxella catarrhalis* is a gram-negative bacterial pathogen causing otitis media in children; sinusitis and conjunctivitis in children and adults; and lower respiratory tract infections, septicemia, and meningitis in immunocompromised hosts. *M. catarrhalis* htrB mutants can be produced and identified. One skilled in the art, using the htrB gene of *H. influenzae*, can isolate the htrB gene of *M. catarrhalis*, and produce a mutated htrB gene (unable to encode functional HtrB) using transposon mutagenesis with subsequent recombination resulting in an *M. catarrhalis* htrB mutant lacking one or more secondary acyl chains. Alternatively, there may be sufficient homology between *M. catarrhalis* and *H. influenzae* to use plasmids pB28 and pB29, each with a mini-Tn3 transposon containing the chloramphenicol acetyltransferase (CAT) gene inserted into the htrB open reading frame at a different location, to transform *M. catarrhalis* for recombination of the mutant htrB gene into the *M. catarrhalis* htrB gene. *M. catarrhalis* transformants are then selected for by growth in the presence of chloramphenicol (1.5 μg/ml), resulting in identification of *M. catarrhalis* htrB mutant strains. Locations of the mTn3 insertion in the chromosomes of the *M. catarrhalis* htrB mutants may be confirmed by genomic Southern hybridization using a probe containing htrB sequences. The resultant *M. catarrhalis* htrB mutants can then be tested for substantially reduced toxicity using assays described by those skilled in the art for measuring the toxic effects induced by endotoxin.

Using the methods according to the present invention, as illustrated in Examples 4 & 5, *M. catarrhalis* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *M. catarrhalis* are known to those skilled in the art.

*M. catarrhalis* contains a natural transformation process (Juni, 1977, *J Clin Microbiol* 5:227–35) and can also be made competent or be electroporated using techniques known to those skilled in the art.

EXAMPLE 10

*Salmonella* htrB Mutants as Immunogens

In another embodiment, the mutant is a *Salmonella* htrB mutant. *Salmonella* species comprise gram-negative bacteria that can cause a variety of clinical illnesses in humans and animals. For example, *S. typhi* is the causative agent of typhoid fever in humans. *S. paratyphi* is a causative organism of a fever known as salmonella fever in humans. Salmonellosis, a gastroenteritis in humans, can be caused by various species in the genus *Salmonella* (*typhimurium, newport, heidelberg,* and *enteritidis*). *Salmonella* htrB mutants can be produced and identified. One skilled in the art, using the htrB gene of *H. influenzae*, can isolate the htrB gene of *Salmonella* species, and produce a mutated htrB gene (unable to encode functional HtrB) using transposon mutagenesis with subsequent recombination resulting in an *Salmonella* htrB mutant lacking one or more secondary acyl chains. Alternatively, there may be sufficient homology between *Salmonella* and *H. influenzae* to use plasmids pB28 and pB29, each with a mini-Tn3 transposon containing the chloramphenicol acetyltransferase (CAT) gene inserted into the htrB open reading frame at a different location, to transform *Salmonella* for recombination of the mutant htrB gene into the *Salmonella* htrB gene. *Salmonella* transformants are then selected for by growth in the presence of chloramphenicol (1.5 μg/ml), resulting in identification of *Salmonella* htrB mutant strains. Locations of the mTn3 insertion in the chromosomes of the *Salmonella* htrB mutants may be confirmed by genomic Southern hybridization using a probe containing htrB sequences. The resultant *Salmonella* htrB mutants can then be tested for substantially reduced toxicity using assays described by those skilled in the art for measuring the toxic effects induced by endotoxin.

Using the methods according to the present invention, as illustrated in Examples 4 & 5, *Salmonella* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *Salmonella* are known to those skilled in the art, and includes:

pYA260 containing lacZ cloned into a trc promoter; and pJW270 conferring tetracycline resistance and containing lacI (Ervin et al., 1993 *Microb Pathogen* 15:93–101).

pB7 confers kanamycin and chloramphenicol resistance, and contains a cloning site flanked by a BalI site and a HindIII site (Purcell et al., 1983, *Infect Immun* 39:1122–1127).

pACK5 contains the replicon of pAC1 from *Acetobacter pasteurianus* and confers kanamycin resistance (Grones et al., 1995, *Biochem Biophys Res Commun* 206:942–947).

pVAC468 is a suicide vector for chromosomal insertion of heterologous antigens into *Salmonella* and contains a polylinker having the following restriction sites: ClaI, EcoRV, XhoI, SacI, SalI, SmaI, XbaI, and BglII (Hohmann et al., 1995, *Proc Natl Acad Sci USA* 92:2904–2908).

Also disclosed is a bacteriophage system, a 'chromosomal expression vector' for inserting genes encoding foreign antigens into the chromosome of *Salmonella*, which uses a defective transposable element carried on bacteriophage lambda (Flynn et al., 1990, *Mol Microb* 4:2111–2118). *Salmonella* can also be made competent (see for example, Purcell et al., 1983, supra) or be electroporated using techniques known to those skilled in the art (see for example, Grones et al., 1995, supra; Coulson et al., 1994, supra).

EXAMPLE 11

*Shigella* htrB Mutants as Immunogens

In another embodiment, the mutant is a *Shigella* species htrB mutant. Members of the genus *Shigella* are gram-negative bacteria which cause diseases such as dysentery (pathogenic species include *dysenteriae, sonnei,* and *flexneri*) primarily in humans. *Shigella* htrB mutants can be produced and identified. One skilled in the art, using the htrB gene of *H. influenzae,* can isolate the htrB gene of *Shigella,* and produce a mutated htrB gene (unable to encode functional HtrB) using transposon mutagenesis with subsequent recombination resulting in an *Shigella* htrB mutant lacking one or more secondary acyl chains. Alternatively, there may be sufficient homology between *Shigella* and *H. influenzae* to use plasmids pB28 and pB29, each with a mini-Tn3 transposon containing the chloramphenicol acetyltransferase (CAT) gene inserted into the htrB open reading frame at a different location, to transform *Shigella* for recombination of the mutant htrB gene into the *Shigella* htrB gene. *Shigella* transformants are then selected for by growth in the presence of chloramphenicol (1.5 µg/ml), resulting in identification of *Shigella* htrB mutant strains. Locations of the mTn3 insertion in the chromosomes of the *Shigella* htrB mutants may be confirmed by genomic Southern hybridization using a probe containing htrB sequences. The resultant *Shigella* htrB mutants can then be tested for substantially reduced toxicity using assays described by those skilled in the art for measuring the toxic effects induced by endotoxin.

Using the methods according to the present invention, as illustrated in Examples 4 & 5, *Shigella* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *Shigella* are known to those skilled in the art, and includes:

pACK5 contains the replicon of pAC1 from *Acetobacter pasteurianus* and confers kanamycin resistance (Grones et al., 1995, supra). *Shigella* can also be made competent or be electroporated using techniques known to those skilled in the art.

EXAMPLE 12

*Pseudomonas aeruginosa* htrB Mutants as Immunogens

In another embodiment, the mutant is a *Pseudomonas aeruginosa* htrB mutant. *Pseudomonas aeruginosa* is a gram-negative bacterial pathogen which cause diseases such as respiratory tract infections and sepsis, particularly in immunocompromised patients. Other pathogenic species for humans and animals include *pseudomallei,* and *mallei*. Mass spectrometry and nuclear magnetic resonance spectroscopy were used to determine the structure of lipid A of *Pseudomonas aeruginosa* LPS. The structure of *P. aeruginosa* lipid A was found to be the same as *Enterobacterial* lipid A: a backbone of a glucosamine disaccharide which is either monophosphorylated or diphosphorylated (positions 1 and 4'); and which carries several molecules of ester- and amide-bound fatty acids. In addition to the hexaacyl and pentaacyl lipid A species, a tetraacyl species was identified (Karunaratne et al., 1992, *Arch Biochem Biophys* 299:368–76).

*Pseudomonas aeruginosa* htrB mutants can be produced and identified. One skilled in the art, using the htrB gene of *H. influenzae,* can isolate the htrB gene of *Pseudomonas aeruqinosa,* and produce a mutated htrB gene (unable to encode functional HtrB) using transposon mutagenesis with subsequent recombination resulting in a *P. aeruginosa* htrB mutant lacking one or more secondary acyl chains. Alternatively, there may be sufficient homology between *P. aeruginosa* and *H. influenzae* to use plasmids pB28 and pB29, each with a mini-Tn3 transposon containing the chloramphenicol acetyltransferase (CAT) gene inserted into the htrB open reading frame at a different location, to transform *P. aeruginosa* for recombination of the mutant htrB gene into the *P. aeruginosa* htrB gene. *P. aeruginosa* transformants are then selected for by growth in the presence of chloramphenicol (1.5 µg/ml), resulting in identification of *P. aeruginosa* htrB mutant strains. Locations of the mTn3 insertion in the chromosomes of the *P. aeruginosa* htrB mutants may be confirmed by genomic Southern hybridization using a probe containing htrB sequences. The resultant *P. aeruginosa* htrB mutants can then be tested for substantially reduced toxicity using assays described by those skilled in the art for measuring the toxic effects induced by endotoxin.

Using the methods according to the present invention, as illustrated in Examples 4 & 5, *P. aeruqinosa* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *P. aeruginosa* are known to those skilled in the art, and includes:

pPAH121 confers carbenicillin resistance, and contains a unique HpaI restriction site (Hoyne et al., 1992, *J Bacteriol* 174:7321–7327.

*P. aeruginosa* can also be made competent (see for example, Hoyne et al., 1992, supra) or be electroporated using techniques known to those skilled in the art.

EXAMPLE 12

Multivalent htrB Mutant Vaccine Formulation

In one embodiment according to the present invention, as illustrated in Examples 4 & 5, the htrB mutant is genetically engineered to express one or more heterologous microbial antigens in producing a multivalent vaccine using methods known to those skilled in the art. In a preferred embodiment, a microbial pathogen may include a respiratory pathogen selected from the group of pathogens, with respective antigens, in Table 1.

TABLE 1

| PATHOGEN | INFECTION/DISEASE | PROTEIN ANTIGEN |
|---|---|---|
| *H. influenzae* | otitis media, lower respiratory tract | D-15, P1, P6[1] |
| Group A *Streptococcus* | pharyngitis, rheumatic fever | M[2] |
| *Branhamella catarrhalis* | otitis media, lower respiratory tract | CD, E[3] |
| *Streptococcus pneumoniae* | pneumonia, otitis media, meningitis | autolysin, pneumolysin[4] |
| *Bordetella pertussis* | pertussis (whooping cough) | filamentous hemagglutinin, pertussis toxin, 69kDa Omp[5] |
| *Pseudomonas aeruginosa* | respiratory tract | Omp OprF, exotoxin A[6] |
| *Legionella pneumophila* | pneumonia | OmpS, Hsp60[7] |
| *Mycoplasma pneumoniae* | upper and lower respiratory tract | P1[8] |
| Respiratory syncytial virus | lower respiratory tract | M2, P, F, G[9] |
| Influenza virus | influenza | HA, M[10] |
| Adenovirus | common cold | |
| rhinovirus | common cold | VP1, VP2, VP3[11] |
| Parainfluenza virus | common cold | HN, F[12] |

TABLE 1-continued

| PATHOGEN | INFECTION/DISEASE | PROTEIN ANTIGEN |
|---|---|---|
| *Pneumocystis carinii* | pneumonia in AIDS | msg[13] |

[1](Flack et al., 1995 Gene 156:97–99; Panezutti et al., 1993, 61:1867–1872; Nelson et al., 1988, Rev Infect Diseases 10:S331–336).
[2](Pruksakorn et al., 1994, Lancet 344:639–642; Dole et al., 1993 J Immunol 151:2188–94).
[3](Murphy et al., 1989, Infect Immun 57:2938–2941; Faden et al., 1992, Infect Immun 60:3824–3829 ).
[4](Lock et al., 1992, Microb Pathog 12:137–143).
[5](Novotny et al., 1991, Dev Biol Stand 73:243–249; Lipscombe et al., 1991 Mol Microbiol 5:1385–1392; He et al., 1993 Eur J Clin Microbial Infect Dis 12:690–695).
[6](Rawling et al., 1995, Infect Immun 63:38–42; Pennington et al., 1988 J Hosp Infect 11A:96–102).
[7](Weeratna et al., 1994, Infect Immun 62:3454–3462).
[8](Jacobs et al., 1990, Infect Immun 58:2464–2469; 1990, J Clin Microbiol 28:1194–1197).
[9](Kulkarni et al., 1995, J Virol 69:1261–1264; Leonov et al., 1994, J Gen Virol 75:1353–1359; Garcia et al., 1993, Virology 195:239–242; Vaux-Peretz et al., 1992, Vaccine 10:113–118).
[10](Kaly et al., 1994, Vaccine 12:753–760; Bucher et al., 1980, J Virol 36:586–590).
[11](Francis et al., 1987, J Gen Virol 68:2687–2691).
[12](Morein et al., 1983, J Gen Virol 64:1557–1569).
[13](Garbe et al., 1994, Infect Immun 62:3092–3101).

In another preferred embodiment, a microbial pathogen may include a pathogen causing a sexually transmitted disease selected from the group of pathogens, with respective antigens, in Table 2.

TABLE 2

| PATHOGEN | INFECTION/DISEASE | PROTEIN ANTIGEN |
|---|---|---|
| *N. gonorrhoeae* | gonorrhea | IgA1 protease[1], PIB[2], H.8[3], Por[4] |
| *Chlamydia trachomatis* | nongonococcal urethritis | MOMP[5], HSP[6] |

[1](Lomholt et al., 1994, Infect Immun 62:3178–83).
[2](Heckels et al., 1990, Vaccine 8:225–230).
[3](Blacker et al., 1985, J Infect Dis 151:650–657).
[4](Wetzler et al., 1992, Vaccine 8:225–230).
[5](Campos et al., 1995, Ophthamol Vis Sci 36:1477–91; Murdin et al., 1995, Infect Immun 63:1116–21).
[6](Taylor et al., 1990, Infect Immun 58:3061–3).

Tables 1 & 2, and the references footnoted which are herein incorporated by reference, illustrate various protein antigens, or peptides thereof, viewed by those skilled in the art to be useful as vaccine candidates against the respective microbial pathogen. Typically, the immunopotency of an epitope, whether from a protein or peptide, of a microbial pathogen is determined by monitoring the immune response of an animal following immunization with the epitope and/or by analyzing human convalescent sera in conjunction with pre-immune sera. Thus, one skilled in the art can determine protein or peptide antigens from microbial pathogens which would be desired to include as a heterologous antigen to be expressed by an htrB mutant according to the present invention. A corresponding nucleic acid sequence, the encoding sequence, can then be deduced from the amino acid sequence of the protein or peptide antigen, wherein the encoding sequence is introduced into the htrB mutant for expression.

EXAMPLE 13

Use of htrB Mutants to Generate Antisera

The htrB mutant, or endotoxin purified therefrom, can be used to generate endotoxin-specific antisera, directed to the particular gram-negative bacterial pathogen, which can be used in an immunoassay to detect the antigen (that particular gram-negative bacterial pathogen), present in the body fluid of an individual suspected of having an infection caused by that gram-negative bacterial pathogen. The body fluid(s) collected for analysis depend on the microorganism to be detected, the suspected site of infection, and whether the body fluid is suspected of containing the antigen or containing antisera. With those considerations in mind, the body fluid could include one or more of sputum, blood, cerebrospinal fluid, lesion exudate, swabbed material from the suspected infection site, and fluids from the upper respiratory tract. Immunoassays for such detection comprises any immunoassay known in the art including, but not limited to, radioimmunoassay, ELISA, "sandwich" assay, precipitin reaction, agglutination assay, fluorescent immunoassay, and chemiluminescence-based immunoassay.

Alternatively, where an immunocompromised individual is suffering from a potentially life-threatening infection caused by a particular gram-negative bacterial pathogen, immunization may be passive, i.e. immunization comprising administration of purified human immunoglobulin containing antibody against an htrB mutant or isolated htrB endotosin of that particular gram-negative bacterial pathogen.

It should be understood that while the invention has been described in detail herein, the examples were for illustrative purposes only. Other modifications of the embodiments of the present invention that are obvious to those skilled in the art of molecular biology, medical diagnostics, and related disciplines are intended to be within the scope of the appended claims.

What is claimed is:

1. A method of making a mutant endotoxin comprising: culturing a non-typeable *Haemophilus influenzae* strain having a mutation in htrB gene, wherein the htrB mutation produces a mutant non-typeable *Haemophilus influenzae* having a mutant endotoxin containing a decreased phosphoethanolamine content and an increased hexose content in the mutant endotoxin's inner core, and a pentaacylated or tetraacylated lipid A lacking one or two secondary acyl chains compared to the corresponding wild-type non-typeable *Haemophilus influenzae* hexaacylated endotoxin, and wherein the mutant endotoxin has substantially reduced toxicity as compared to the hexaacylated endotoxin of the wild-type non-typeable *Haemophilus influenzae*; and purifying the mutant endotoxin.

2. A mutant endotoxin made according to the method of claim 1.

3. A method of making a mutant non-typeable *Haemophilus influenzae* comprising mutating htrB gene within a wild-type non-typeable *Haemophilus influenzae*, wherein the htrB mutation produces a mutant non-typeable *Haemophilus influenzae* having a mutant endotoxin containing a decreased phosphoethanolamine content and an increased hexose content in the mutant endotoxin's inner core, and a pentaacylated or tetraacylated lipid A lacking one or two secondary acyl chains compared to the corresponding wild-type non-typeable *Haemophilus influenzae* hexaacylated endotoxin, and wherein the mutant endotoxin has substantially reduced toxicity as compared to the hexaacylated endotoxin of the wild-type non-typeable *Haemophilus influenzae*.

4. The mutant endotoxin made according to the method of claim 1, wherein the mutant endotoxin is purified form the mutant non-typeable *Haemophilus influenzae* by phenol-water extraction or proteinase digestion.

5. The mutant non-typeable *Haemophilus influenzae* made according to the method of claim 3.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 969 nucleotides
      (B) TYPE: nucleic acid
      (C) STRANDEDNESS: double-stranded
      (D) TOPOLOGY: linear (ii) MOLECULE TYPE: genomic DNA (iii) HYPOTHETICAL: yes (iv) ORIGINAL SOURCE:
    (A) ORGANISM: H. influenzae
    (B) STRAIN: 2019
    (C) CELL TYPE: bacterium (v) SEQUENCE DESCRIPTION: SEQ ID NO:1:

```
TAAACTACGC CCCTAACTTA CGTGGAAAGA ACA ATG AAA AAC GAA AAA CTC            51
                                    Met Lys Asn Glu Lys Leu
                                      1               5

CCT CAA TTT CAA CCG CAC TTT TTA GCC CCA AAA TAC TGG CTT TTT            96
Pro Gln Phe Gln Pro His Phe Leu Ala Pro Lys Tyr Trp Leu Phe
             10                  15                  20

TGG CTA GGC GTG GCA ATT TGG CGA AGT ATT TTA TGT CTT CCC TAT           141
Trp Leu Gly Val Ala Ile Trp Arg Ser Ile Leu Cys Leu Pro Tyr
                 25                  30                  35

CCT ATT TTG CGC CAT ATT GGT CAT GGT TTC GGT TGG CTG TTT TCA           186
Pro Ile Leu Arg His Ile Gly His Gly Phe Gly Trp Leu Phe Ser
                 40                  45                  50

CAT TTA AAA GTG GGT AAA CGT CGA GCT GCC ATT GCA CGC CGT AAT           231
His Leu Lys Val Gly Lys Arg Arg Ala Ala Ile Ala Arg Arg Asn
             55                  60                  65

CTT GAA CTT TGT TTC CCT GAT ATG CCT GAA AAC GAA CGT GAG ACG           276
Leu Glu Leu Cys Phe Pro Asp Met Pro Glu Asn Glu Arg Glu Thr
             70                  75                  80

ATT TTG CAA GAA AAT CTT CGT TCA GTA GGC ATG GCA ATT ATC GAA           321
Ile Leu Gln Glu Asn Leu Arg Ser Val Gly Met Ala Ile Ile Glu
             85                  90                  95

ACT GGC ATG GCT TGG TTT TGG TCG GAT TCA CGT ATC AAA AAA TGG           366
Thr Gly Met Ala Trp Phe Trp Ser Asp Ser Arg Ile Lys Lys Trp
                100                 105                 110

TCG AAA GTT GAA GGC TTA CAT TAT CTA AAA GAA AAT CAA AAA GAT           411
Ser Lys Val Glu Gly Leu His Tyr Leu Lys Glu Asn Gln Lys Asp
            115                 120                 125

GGA ATT GTT CTC GTC GGC GTT CAT TTC TTA ACG CTA GAA CTT GGC           456
Gly Ile Val Leu Val Gly Val His Phe Leu Thr Leu Glu Leu Gly
            130                 135                 140

GCA CGC ATC ATT GGT TTA CAT CAT CCT GGC ATT GGT GTT TAT CGT           501
Ala Arg Ile Ile Gly Leu His His Pro Gly Ile Gly Val Tyr Arg
            145                 150                 155

CCA AAT GAT AAT CCT TTG CTT GAT TGG CTA CAA ACA CAA GGC CGT           546
Pro Asn Asp Asn Pro Leu Leu Asp Trp Leu Gln Thr Gln Gly Arg
            160                 165                 170

TTA CGC TCC AAT AAA GAT ATG CTT GAT CGT AAA GAT TTA CGC GGA           591
Leu Arg Ser Asn Lys Asp Met Leu Asp Arg Lys Asp Leu Arg Gly
            175                 180                 185

ATG ATC AAA GCT TTA CGC CAC GAA GAA ACC ATT TGG TAT GCG CCT           636
Met Ile Lys Ala Leu Arg His Glu Glu Thr Ile Trp Tyr Ala Pro
            190                 195                 200

GAT CAC GAT TAC GGC AGA AAA AAT GCC GTT TTT GTT CCT TTT TTT           681
Asp His Asp Tyr Gly Arg Lys Asn Ala Val Phe Val Pro Phe Phe
            205                 210                 215

GCA GTA CCT GAC ACT TGC ACT ACT ACT GGT AGT TAT TAT TTA TTG           726
Ala Val Pro Asp Thr Cys Thr Thr Thr Gly Ser Tyr Tyr Leu Leu
            220                 225                 230

AAA TCC TCG CAA AAC AGC AAA GTG ATT CCA TTT GCG CCA TTA CGC           771
Lys Ser Ser Gln Asn Ser Lys Val Ile Pro Phe Ala Pro Leu Arg
            235                 240                 245

AAT AAA GAT GGT TCA GGC TAT ACC GTG AGC ATT TCA GCG CCT GTT           816
Asn Lys Asp Gly Ser Gly Tyr Thr Val Ser Ile Ser Ala Pro Val
            250                 255                 260
```

```
                                                    -continued
GAT TTT ACA GAT TTA CAA GAT GAA GTA GCG ATA GCT GTG CGA ATG                861
Asp Phe Thr Asp Leu Gln Asp Glu Val Ala Ile Ala Val Arg Met
            265                 270                 275

AAT CAA ATC GTT GAA AAG GAA ATC ATG AAG GGC ATA TCA CAA TAT                906
Asn Gln Ile Val Glu Lys Glu Ile Met Lys Gly Ile Ser Gln Tyr
            280                 285                 290

ATG TGG CTA CAT CGT CGT TTT AAA ACA CGC CCC GAT GAA AAT ACG                951
Met Trp Leu His Arg Arg Phe Lys Thr Arg Pro Asp Glu Asn Thr
            295                 300                 305

CCT AGT TTA TAC GAT TAA                                                    969
Pro Ser Leu Tyr Asp
            310

(2) INFORMATION FOR SEQ ID NO:2:

(i) SEQUENCE CHARACTERISTICS:
        (A) LENGTH: 31 nucleotides
        (B) TYPE: nucleic acid
        (C) STRANDEDNESS: single-stranded
        (D) TOPOLOGY: linear (ii) ORIGINAL SOURCE:
        (A) ORGANISM: H. influenzae
        (B) STRAIN: 2019

(iii) IMMEDIATE SOURCE: synthesized (iv) SEQUENCE DESCRIPTION: SEQ ID NO:2:

CCAATATGGC GCAAAATAGG ATAGGGAAGA C                                          31

(2) INFORMATION FOR SEQ ID NO:3:

(i) SEQUENCE CHARACTERISTICS:
        (A) LENGTH: 9 nucleotides
        (B) TYPE: nucleic acid
        (C) STRANDEDNESS: single-stranded
        (D) TOPOLOGY: linear (ii) ORIGINAL SOURCE:
        (A) ORGANISM: H. influenzae (iii) FEATURE:
        (A) OTHER INFORMATION: uptake sequence for transformation (iv) SEQUENCE DESCRIPTION: SEQ ID NO:3:

AAGTGCGGT                                                                    9
```